US006284233B1

(12) United States Patent
Simon et al.

(10) Patent No.: US 6,284,233 B1
(45) Date of Patent: *Sep. 4, 2001

(54) ANTIWRINKLE COMPOSITION COMPRISING A COMBINATION OF TIGHTENING POLYMERS OF SYNTHETIC AND/OR NATURAL ORIGIN AND OF DENDRITIC POLYESTERS

(75) Inventors: Pascal Simon, Vitry sur Seine; Veronique Chevalier, Villecresnes, both of (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/397,521

(22) Filed: Sep. 17, 1999

(30) Foreign Application Priority Data

Sep. 17, 1998 (FR) .................................................. 98 11635

(51) Int. Cl.$^7$ ............................ A61K 31/74; C08F 20/00; C08G 63/78; C08G 63/00; C08G 63/48
(52) U.S. Cl. ..................... 424/78.03; 424/401; 424/70.1; 424/60; 424/61; 424/62; 424/63; 424/70.11; 424/78.02; 424/78.03; 424/78.17; 424/78.08; 424/DIG. 2; 424/DIG. 3; 424/DIG. 16; 514/778.1; 514/844; 514/845; 514/846; 514/847; 514/848; 514/858; 514/859; 514/860; 514/861; 514/862; 514/863; 514/864; 514/865; 514/881; 514/887; 514/937; 514/944; 514/945; 514/772.1; 514/784; 523/122; 525/437; 525/444; 525/444.5; 525/445; 525/450; 525/242; 528/271; 528/274; 528/295.5
(58) Field of Search ..................... 424/78.03, 400, 424/401, 70.1, 60, 62, 63, 61, 70.11, 78.02, 78.17, 78.08, DIG. 2, DIG. 3, DIG. 16; 514/788.1, 844–848, 858–865, 881, 887, 937, 944, 945, 772.1, 784; 523/122; 525/437, 444, 444.5, 495, 450, 242; 528/271, 274, 295.5

(56) References Cited

U.S. PATENT DOCUMENTS 5,530,092 * 6/1996 Meijer et al. ........................ 528/363
6,001,367 * 12/1999 Bazin et al. ...................... 424/195.1

FOREIGN PATENT DOCUMENTS 2 758 083    7/1998 (FR) .
93/17060    9/1993 (WO) .

OTHER PUBLICATIONS

Grant & Hackh's Chemical Dictionary, Roger Grant & Claire Grant, 5th Ed., McGraw–Hill Book Company, 1987, p294.*

* cited by examiner

*Primary Examiner*—Diana Dudash
*Assistant Examiner*—Jean-Michel Campagne
(74) *Attorney, Agent, or Firm*—Oblon, Spivak, McClelland, Maier & Neustadt, P.C.

(57) ABSTRACT

The present invention relates to an antiwrinkle composition that includes, in a physiologically acceptable medium:

a dispersion of a film-forming polymeric system containing at least one polymer capable of forming a film permeable to water vapor, having a Young's modulus ranging from $10^8$ to $10^{10}$ N/m$^2$ and producing, after application at a concentration of 7% in water and then drying, a retraction of the isolated *stratum corneum* greater than 1% at a temperature of 30° C. and a relative humidity of 40%, and a dendritic polyester polymer having terminal hydroxyl functional groups.

27 Claims, No Drawings

ANTIWRINKLE COMPOSITION COMPRISING A COMBINATION OF TIGHTENING POLYMERS OF SYNTHETIC AND/OR NATURAL ORIGIN AND OF DENDRITIC POLYESTERS

BACKGROUND OF THE INVENTION

1. Field of the Invention

The present invention relates to antiwrinkle cosmetic or dermatological compositions containing polymers with a "tightening" effect combined with dendritic polyesters, a method of cosmetic treatment using these compositions as well as the use of the combination of a film-forming polymeric system having a "tightening" effect and a dendritic polyester for the manufacture of cosmetic or dermatological compositions intended for reducing and/or removing wrinkles and/or fine lines on the skin by a tightening effect.

2. Discussion of the Background

The process of skin ageing is accompanied by a gradual modification of the skin structure and functions. The principal clinical signs of skin ageing are the appearance of wrinkles and fine lines, which increase with age.

It is known to correct these signs of ageing by using cosmetic or dermatological compositions that contains active ingredients such as α-hydroxy acids, β-hydroxy acids and retinoids. These active ingredients are believed to act on the wrinkles by eliminating the dead cells and by accelerating the process of cell renewal. However, the visible effect of these compositions occurs only after a certain period of application, which may range from a few days to several weeks.

One approach for solving this problem consists in using so-called "tightening" agents which, through an effect of tightening of the superficial layer of the skin, are capable of making the skin smooth by reducing the number and depth of the wrinkles and fine lines and of making fatigue marks disappear, this being achieved instantly.

The "tightening agents" noted above are polymers of natural or synthetic origin which are capable of forming a film which causes the retraction of the *stratum corneum*, the superficial horny layer of the epidermis.

The cosmetic or dermatological use of such polymeric systems to attenuate the effects of skin ageing is described in Patent Applications FR-2,758,083 and FR-2,758,084. These tightening polymeric systems, though very effective and rapid, sometimes cause, nevertheless, a feeling of discomfort in some users, in particular those having fragile skin. These tightening agents indeed form on the skin a film which is too rigid and not very flexible. The problem of seeking to obtain a high tightening effect by using smaller quantities of tightening polymers was thus posed.

The Applicant has discovered, surprisingly, that by combining dendritic polyesters with terminal hydroxyl groups which, by themselves, have no epidermis-tightening power, with known polymeric tightening systems, it is possible to significantly reinforce the tightening effect of the latter.

SUMMARY OF THE INVENTION

The subject of the present invention therefore relates to antiwrinkle cosmetic or dermatological compositions containing a film-forming polymeric system containing at least one polymer with "tightening" effect, of natural and/or synthetic origin, and a dendritic polyester with terminal hydroxyl groups.

The subject of the invention also relates to a method of treatment of the skin with the above antiwrinkle cosmetic compositions, as well as the use of the combination of a film-forming polymeric system with "tightening" effect and of a dendritic polyester for the manufacture of cosmetic or dermatological compositions intended for reducing and/or removing the wrinkles and/or the fine lines on the skin.

Accordingly, one embodiment of the invention provides an antiwrinkle cosmetic or dermatological composition, that includes in a physiologically acceptable medium:

a dispersion of a film-forming polymeric system including at least one polymer capable of forming a film permeable to water vapour, having a Young's modulus ranging from $10^8$ to $10^{10}$ N/m² and producing, after application at a concentration of 7% in water and then drying, a retraction of the isolated *stratum corneum* greater than 1% at a temperature of 30° C. and at a relative humidity of 40%, and a dendritic polyester polymer having terminal hydroxyl functional groups.

Another embodiment of the invention provides a method of treatment of the skin comprising applying to the skin of the face, the neck and/or the cleavage the antiwrinkle composition above.

Another embodiment of the invention provides a cosmetic that includes the antiwrinkle composition for reducing and/or removing the wrinkles and/or fine lines on the skin by a tightening effect.

Another embodiment of the invention provides a method for the preparation of a cosmetic or dermatological composition intended for reducing and/or removing the wrinkles and/or fine lines on the skin, that includes combining:

a dispersion of a film-forming polymeric system containing at least one polymer capable of forming a film permeable to water vapour, having a Young's modulus ranging from $10^8$ to $9 \times 10^{10}$ N/m² and producing, after application at a concentration of 7% in water and then drying, a retraction of the isolated *stratum corneum* greater than 1% at a temperature of 30° C. and a relative humidity of 40%, and a dendritic polyester polymer having terminal hydroxyl functional groups, to prepare a cosmetic or dermatological composition intended for reducing and/or removing the wrinkles and/or fine lines on the skin.

DESCRIPTION OF THE PREFERRED EMBODIMENTS

Various other objects, features and attendant advantages of the present invention will be more fully appreciated as the same becomes better understood from the following detailed description, which is not intended to be limiting unless otherwise specified.

Preferably, the cosmetic effect of the compositions of the present invention is based on their skin "tightening" power. This "tightening" power is defined according to the present invention as the capacity of a homogeneous film formed on the isolated *stratum corneum* to cause a retraction of at least 1% and preferably of at least 1.3% thereof at a temperature of 30° C. and for a relative humidity of 40%. Preferably, this film is formed by applying and drying an aqueous dispersion containing 7% of the said film-forming polymeric system. To determine the tightening effect, the length of the *stratum corneum* sample before treatment and that obtained after treatment, that is to say after application of the polymer, are measured. The tightening effect is characterized by the reduction in the length of the sample after treatment, divided by the initial length of the sample before treatment, according to the equation:

$$\text{tightening effect} = 100 \times l_1 - l_0 / l_0 \%$$

wherein $l_1$ is the length after treatment and $l_0$ is the length before treatment.

The length of the sample is measured with the "miniature tensile tester MTT 610" apparatus.

The name "film-forming" polymer according to the present invention applies to any polymer or polymeric system capable of forming, after application to a glass plate and drying, a continuous film which does not form scales or cracks as judged by the ordinary standards.

The film formed by the tightening polymeric system contained in the antiwrinkle compositions of the present invention should have a modulus of elasticity (Young's modulus determined by instrument micro- or nano-indentation methods; ASTM E384–89 standard) ranging from $10^8$ to $10^{10}$ N/m$^2$ and preferably from 6.5 to $9 \times 10^9$ N/m$^2$. The modulus of elasticity values within this interval are 10 to 100 times higher than that for the *stratum corneum*. Such a modulus of elasticity therefore makes it possible for the polymeric film to follow perfectly the deformations of the skin, which results both in a persistent efficacy and good comfort during use due to the absence of a feeling of excessive pulling.

The film formed on the epidermis should, moreover, be permeable to water vapour so as not to impede skin perspiration. The permeability of the film is evaluated by measuring the Insensitive Water Loss (IWL) from defatted *stratum corneum* treated with the polymer. When the film is sufficiently permeable to water vapour, the IWL is not modified. The measurement of the IWL is carried out conventionally with the aid of an evaporimeter (Servomed) which allows a quantitative determination of the evaporation of water, that is to say of the transport of water by diffusion on a *stratum corneum* sample obstructing a cylindrical capsule containing water, the whole being placed in a chamber at controlled temperature and relative humidity. Sensors make it possible to measure the partial pressure of water vapour at two points situated at different distances on the sample. The water vapour partial pressure gradient is thus determined between the two points, and therefore the rate of evaporation in accordance with Fick's law.

The film-forming tightening polymers meeting the elasticity, retraction and water vapour permeability criteria described above include polymers of natural origin and/or of synthetic origin, and combinations thereof.

Among the preferred natural polymers with tightening effect, there may be mentioned the polymers of plant origin, the polymers derived from superficial body growths, egg proteins, latexes of natural origin and polysaccharides, and combinations thereof.

The preferred polymers of plant origin include, for example, the protein extracts of cereals, legumes and oilseeds such as extracts of maize, rye, wheat, buckwheat, sesame, spelt, pea, broadbean, lentil, soyabean and lupin. As preferred proteins, there may be mentioned, for example, the protein extract of soyabean sold by the company ISD under the name PROFAM972 or by the company LSN under the name ELESERYL, or the protein fraction of white lupin.

Preferred polymers derived from superficial body growths include any polymer obtained from body hair, nails, carapaces of insects or of crustaceans, head hair, feathers, beaks, hoofs and crests of animals. There may be mentioned, for example, chitin and its derivatives, in particular chitosan, as well as chitosan derivatives such as hydroxypropylchitosan, the succinylated derivative of chitosan, chitosan lactate, chitosan glutamate or carboxymethylchitosan succinamide, or alternatively keratin derivatives such as keratin hydrolysates and sulphonic keratins.

Egg albumin may be mentioned as a preferred egg protein.

Preferred natural latexes include, for example, shellac resin, sandarac gum, dammars, elemis, copals, cellulose derivatives and mixtures of these polymers.

Preferred polysaccharides include, for example, guar gum, optionally modified with anionic groups such as carboxylate or phosphate, xanthan gum, alginates.

The film-forming tightening polymers of synthetic origin are preferably provided in the form of a latex or a pseudolatex.

A latex is an aqueous suspension of particles of polymers obtained by free-radical polymerization or by polycondensation according to the well-known technique of polymerization in emulsion.

Preferably, pseudolatex is understood to mean an aqueous dispersion of synthetic polymers obtained not by polymerization in emulsion but by dispersion, in water, of polymers previously obtained according to another synthesis technique within the ordinary skill of artisan.

In both cases, the dispersions are preferably stabilized by fillers carried by the polymer. The latex or pseudolatex particles preferably have a size ranging from 10 to 400 nm, preferably from 20 to 350 nm.

Preferably synthetic polymers forming the latex or pseudolatex particles include, for example, anionic, cationic, nonionic or amphoteric polyurethanes, polyurethane-polyacrylics, polyurethane-polyvinylpyrrolidones, polyurethane-polyesters, polyurehiane-polyethers, polyureas, and mixtures thereof.

Preferably, the polyurethane may be, for example, an aliphatic, cycloaliphatic or aromatic polyurethane, polyurea/urethane or polyurea copolymer containing at least one linear or branched aliphatic and/or cycloaliphatic and/or aromatic polyester sequence and/or, at least one aliphatic and/or cycloaliphatic and/or aromatic polyether sequence and/or at least one linear or branched, substituted or unsubstituted silicone sequence, and/or at least one sequence containing fluorinated groups.

The polyurethanes may also be obtained from linear or branched polyesters, or from alkyd resins containing active hydrogen atoms which are modified by reacting with a diisocyanate and a bifunctional organic compound (for example dihydrogen, diamino or hydroxyamine-containing) containing in addition, either a carboxylic acid or carboxylate group, or a sulphonic acid or sulphonate group, or alternatively a tertiary amine group or a quaternary ammonium group.

There may also be mentioned, as more preferred synthetic polymers forming latexes or pseudolatexes, polyesters, poly (ester amides), fatty chain polyesters, polyamides and epoxyester resins.

There may also be mentioned as more preferred anionic comonomers which make it possible to synthesize negatively charged polyurethanes, for example dimethylolpropionic acid, trimellitic acid or anhydride, sodium pentanediol-3-sulphonate or sodium 1,3-dicarboxybenzene-5-sulphonate.

These polymers are described, for example, in the document EP-A-648 485, the entire contents of which are hereby incorporated by reference.

Preferred latexes or pseudolatexes may also include acrylic homopolymers or copolymers, or alternatively of polymers based on sulphonated isophthalic acid.

Preferred film-forming tightening polymers of synthetic origin are marketed, for example, under the names SANCURE 2060 (polyester-polyurethane), SANCURE 2255 (polyester-polyurethane), SANCURE 815 (polyester-polyurethane), SANCURE 878 (polyether-polyurethane) and SANCURE 861 (polyether-polyurethane) by the company SANNCOR, under the names NEOREZ R974 (polyester-polyurethane), NEOREZ R981 (polyester-polyurethane), NEOREZ R970 (polyether-polyurethane) by the company ICI, and under the name NEOCRYL XK-90 (dispersion of an acrylic copolymer) by the company ZENECA.

Among the set of tightening polymers of natural and synthetic origin presented above, polymers having free hydroxyl groups or anionic groups are most particularly preferred.

The film-forming polymeric system may be formed by a mixture of several tightening polymers of natural origin and/or of synthetic origin which are described above. It may, in addition, contain one or more plasticizing agents chosen so as to obtain the desired mechanical characteristics.

The plasticizing agent is not particularly limited and may be chosen from all the compounds known to persons skilled in the art as being capable of fulfilling this function. There may be mentioned, for example, lower alcohols (ethanol, propanol, butanol), glycols and derivatives of glycols such as ethyl or methyl ether of diethylene glycol, ethyl or butyl ether of ethylene glycol, methyl or phenyl ether of propylene glycol, ethyl or butyl ether of dipropylene glycol, butyl or methyl ether of tripropylene glycol; esters of glycerol, esters of acids such as citrates, phthalates, adipates, carbonates, tartrates, phosphates or sebacates; oxyethylenated derivatives such as oxyethylenated oils, for example oxyethylenated castor oil, and oxyethylenated silicone oils; polymers soluble in water or in aqueous dispersion having a glass transition temperature of less than 25° C., preferably less than 15° C.

The quantity of plasticizing agent is not particularly limited, and it may be chosen by persons skilled in the art on the basis of their general knowledge, so as to obtain a polymeric system which leads to a film having the desired mechanical properties, while allowing the composition to retain acceptable cosmetic properties.

Preferably, in the antiwrinkle compositions of the present invention, this film-forming polymer system with a tightening effect, containing one or more polymers of natural and/or synthetic origin and optionally one plasticizing agent, and provided in the form of an aqueous dispersion, is combined with polyesters having a highly branched structure called "dendritic".

Preferable dendritic polymers or dendrimers (from the Greek dendron=tree) include "arborescent", that is to say highly branched, polymer molecules described by D. A. Tomalia and his team at the beginning of the 1990's (Donald A. Tomalia et al, *Angewandte Chemie, Int. Engl. Ed.*, Vol. 29, No. 2, pages 138–175, the entire contents of which are hereby incorporated by reference). They are molecular structures constructed around a generally polyvalent central unit Branched units for chain-extension are linked around this central unit, in concentric layers and according to a perfectly defined structure, thus giving rise to monodispersed symmetric- macromolecules having a well-defined chemical and stereochemical structure.

Preferred dendritic polymers used in the cosmetic or dermatological compositions of the present invention include dendrimers having the chemical structure of a polyester and which end with hydroxyl groups. The structure and the preparation of these polymers is described in WO-A-93/17060, the entire contents of which are hereby incorporated by reference.

More preferably, the dendritic polymers used in the compositions of the present invention may be defined as being highly branched macromolecules of the polyester type, including:

a central unit derived from an initiator compound carrying one or more hydroxyl functions (a), chain-extension units derived from a chain-extension molecule carrying a carboxyl function (b) and at least two hydroxyl functions (c), wherein each of the hydroxyl functions (a) of the central molecule is the starting point of a polycondensation reaction (by esterification) which starts with the reaction of the hydroxyl functions (a) of the central molecule with the carboxyl functions (b) of the chain-extension molecules, and then continues with the reaction of the carboxyl functions (b) with the hydroxyl functions (c) of the chain-extension molecules.

Preferably, the initiator compound carrying one or more hydroxyl functions and forming the central unit around which the dendritic structure will be constructed is a mono-, di- or polyhydroxylated compound. It is preferably chosen from (a) a monofunctional alcohol, (b) an aliphatic, cycloaliphatic or aromatic diol, (c) a triol, (d) a tetrol, (e) a sugar alcohol, (f) anhydro-ennea-heptitol or dipentaeytritol, (g) an α-alkylglycoside, (h) a polyalkoxylated polymer obtained by polyalkoxylation of one of the alcohols (a) to (g), having a molar mass at most equal to 8000.

There may be mentioned, by way of examples, preferred initiator compounds for the; preparation of the dendritic polyesters used in the present invention, which include ditrimethylolpropane, ditrimethylolethane, dipentaeyritol, pentaeryhitol, an alkoxylated pentaerythritol, trimethylolethane, trimethylolpropane, an alkoxylated trimethylolpropane, glycerol, neopentyl glycol, dimethylolpropane or 1,3-dioxane-5,5-dimethanol and combinations thereof.

These hydroxylated initiator compounds forming the central unit of the future dendrimer are reacted preferably with molecules called chain-extension molecules which include diol-monoacid-type compounds chosen from monocarboxylic acids containing at least two hydroxyl functions, and monocarboxylic acids containing at least two hydroxyl functions of which one or more carry a hydroxyalkyl substituent.

Preferred examples of such compounds are dimethylolpropionic acid, α,α-bis(hydroxymethyl)butyric acid, α,α,α-tris(hydroxymethyl)acetic acid, α,α-bis(hydroxymethyl) valeric acid, α,α-bis(hydroxy)propionic acid and 3,5-dihydroxybenzoic acid.

In a particularly preferred embodiment of the present invention, the initiator compound is chosen from ditrimethylolpropane, trimethylolpropane, an ethoxylated pentaerythritol, pentaerythritol or glycerol, and the chain-extension molecule is dimethylolpropionic acid.

The dendritic polymers of the polyester type with terminal hydroxyl functions which are used in the compositions of the present invention are preferably characterized, in addition in that some (at least one) of the terminal hydroxyl functions of the polyester-type dendritic polymer may carry substituents derived from at least one chain-terminating agent.

A polymer without derived substituents may also be preferably used. However, when part of the terminal hydroxyl functions carries a derived substituent, the fraction of these terminal hydroxyl functions carrying a chain-terminating unit is preferably between 1 and 90 mol %, more preferably between 10 and 50 mol % relative to the total number of terminal hydroxyl functions.

The chain-terminating agent is preferably chosen so as to make it possible to modify at will the physicochemical properties of the dendritic polyesters used in the compositions of the present invention.

The above chain-terminating agent is preferably chosen from a wide variety of compounds capable of forming covalent bonds with the terminal hydroxyl functions. These compounds include in particular:

i) a saturated monocarboxylic acid or a saturated fatty acid or an anhydride of such a compound, ii) an unsaturated fatty acid, iii) an unsaturated monocarboxylic acid, iv) a diisocyanate or an oligomer of such a compound, v) an addition product prepared using known methods from a compound according to iv), vi) a dicarboxylic or polycarboxylic acid or an anhydride of such a compound, vii) an addition product prepared using known methods from a compound according to vi), viii) an aromatic monocarboxylic acid, ix) an epihalohydrin, x) a glycidyl ester of a monocarboxylic acid or of a fatty acid containing from 1 to 24 carbon atoms, xi) an epoxide of an unsaturated fatty acid containing from 3 to 24 carbon atoms.

Preferred chain-terminating compounds are particularly lauric acid, linseed fatty acids, soyabean fatty acids, tallow fatty acids, dehydrogenated castor oil fatty acids, caproic acid, caprylic acid, diallyl ether maleate of trimethylolpropane, methacrylic acid and acrylic acid, and mixtures thereof.

Preferred dendritic polymers of the polyester type with terminal hydroxyl functions and optionally carrying chain-terminating groups are known and are marketed by the company PERSTORP.

Particularly preferred polymers used in the present invention include:

a dendritic polyester obtained by polycondensation of dimethylolpropionic acid with trimethylolpropane, free of chain-terminating agents, marketed under the name BOLTORN H40 TMP CORE;

a dendritic polyester obtained by polycondensation of dimethylolpropionic acid with polyoxyethylenated pentaettitol (5 EO units on each hydroxyl function), in which 50% of the hydroxyl functions are esterified with capric/caprylic acid (technical name esterified HBP 3G);

a dendritic polyester obtained by polycondensation of dimethylolpropionic acid with polyoxyethylenated pentaerythritol (5 EO units on each hydroxyl function), free of chain-terminating agent (technical name HBP Polyol 3G), all these polymers being products from the company PERSTORP.

Preferably, the concentration of the dendritic polymer relative to the total composition is within the interval ranging from 0.1 to 5% by weight, more preferably 0.25 to 4% by weight, more preferably 1 to 3% by weight.

Preferably, the film-forming polymeric system is present in an amount of 0.5 to 70% by weight, more preferably 0.5 to 30% by weight, expressed as active material relative to the total composition.

The quantities of dendritic polymer and of tightening polymers will be chosen so that the weight ratio of the dendritic polymer to the film-forming polymeric system is preferably within the interval ranging from $\frac{1}{2}$ to $\frac{1}{100}$, more preferably from $\frac{1}{10}$ to $\frac{1}{50}$.

The antiwrinkle compositions according to the invention may contain, in addition, one or more cosmetic active ingredients chosen from anti-free radical agents, moisturizing agents, vitamins, proteins other than those constituting the tightening system, ceramides, α-hydroxy acids, β-hydroxy acids and retinoids.

They may contain, in addition, cosmetic adjuvants which are customary in cosmetics and in dermatology. These adjuvants are for example solvents, pH-regulating agents, antioxidants, preservatives, pigments and colourings, fillers, emollients, antifoams, fatty substances such as vegetable or animal oils or waxes, silicones, perfumes, surfactants, plasticizers, thickening or gelling polymers, sunscreens and agents imparting softness (allantoin, PVM/MA decadiene copolymer).

As oils which can be used in the composition of the invention, there may be mentioned in particular, for example, oils of plant origin, mineral oils (liquid paraffin), synthetic oils, silicone oils (cyclomethicone) and fluorinated oils. The other fatty substances which may be present in the oily phase may be, for example, fatty acids, fatty alcohols (cetyl alcohol) and waxes.

Of course, persons skilled in the art will be careful to choose this or these possible additional compounds and their quantity such that the advantageous properties intrinsically attached to the cosmetic or dermatological composition in accordance with the invention are not, or not substantially, altered by the addition(s) envisaged.

The antiwrinkle compositions may be provided in any form allowing the formation of a homogeneous film having the desired cosmetic tightening effect. They correspond, for example, to an emulsion such as a cream or a milk, a gel, a lotion, a vesicular dispersion, a serum, a paste or a solid stick.

One preferred embodiments of the present invention also relates to a method of nontherapeutic treatment of the skin which includes applying the compositions described above in a thin layer to the skin of the face, the neck and/or the cleavage.

Another preferred embodiment of the present invention relates to the use of a combination of a dispersion of a film-forming polymeric system containing at least one polymer of natural and/or synthetic origin and capable of forming a film permeable to water vapour, having a Young's modulus ranging from $10^8$ to $10^{10}$ N/m$^2$ and producing, after application at a concentration of 7% in water and then drying, a retraction of the isolated *stratum corneum* greater than 1% at a temperature of 30° C. and for a relative humidity of 40%, and of a dendritic polymer of the polyester type with terminal hydroxyl functions, for the preparation of a cosmetic or dermatological composition intended for reducing and/or a removing the wrinkles and/or fine lines on the skin.

EXAMPLES

Having generally described this invention, a further understanding can be obtained by reference to certain specific examples which are provided herein for purposes of illustration only and are not intended to be limiting unless otherwise specified.

Example 1

| Antiwrinkle cream | |
|---|---|
| cetyl alcohol | 1.5% |
| liquid paraffin | 5% |
| cyclomethicone | 7% |
| sorbitan tristearate (surfactant) | 1.3% |
| PEG 40 stearate (surfactant) | 2.7% |
| soyabean protein (Eleseryl ® marketed by LSN) | 3% |
| Sancure 2060 waterborne urethane (27% of active material in water) | 10% |
| BOLTORN H 40 TMP marketed by PERSTORP | 0.2% |
| ethyl alcohol | 10% |
| perfumes, preservatives | qs |
| demineralized water | qs 100% |

Example 2

| Antiwrinkle cream | |
|---|---|
| cetyl alcohol | 1.5% |
| liquid paraffin | 5% |
| cyclomethicone | 7% |
| sorbitan tristearate (surfactant) | 1.3% |
| PEG 40 stearate (surfactant) | 2.7% |
| protein fraction of white lupin (containing 0.7% of active material) | 30% |
| Sancure 815 (35% of active material in water) | 12% |
| BOLTORN H 40 TMP marketed by PERSTORP | 0.2% |
| ethyl alcohol | 10% |
| perfumes, preservatives | qs |
| demineralized water | qs 100% |

Example 3

| Serum | |
|---|---|
| polyacrylamide/$C_{13}$–$C_{14}$ isoparaffin/laureth-7 (Sepigel ® marketed by SEPPIC) | 1% |
| xanthan gum | 0.2% |
| PVM/MA decadiene copolymer (ANTARON ST 06 marketed by ISP) | 0.2% |
| triethanolamine | 0.2% |
| Sancure 815 (35% of active material in water) | 12% |
| BOLTORN H 40 TMP marketed by PERSTORP | 0.3% |
| ethyl alcohol | 10% |
| perfumes, preservatives | qs |
| demineralized water | qs 100% |

Having now fully described the invention, it will be apparent to one of ordinary skill in the art that many changes and modifications can be made thereto without departing from the spirit or scope of the invention as set forth herein.

This application is based on FR 98 11635, filed Sep. 17, 1998, the entire contents of which are hereby incorporated by reference.

What is claimed is:

1. An antiwrinkle cosmetic or dermatological composition, comprising in a physiologically acceptable medium:
    a dispersion of a film-forming polymeric system comprising at least one polymer capable of forming a film permeable to water vapour, having a Young's modulus ranging from $10^8$ to $10^{10}$ N/m$^2$ and producing, after application at a concentration of 7% in water and then drying, a retraction of the isolated *stratum corneum* greater than 1% at a temperature of 30° C. and a relative humidity of 40%, and
    a dendritic polyester polymer having terminal hydroxyl functional groups.

2. The antiwrinkle composition according to claim 1, wherein the polymer contained in said film-forming polymeric system is a polymer of natural origin.

3. The antiwrinkle composition according to claim 2, wherein the polymer of natural origin is selected from the group consisting of polymers of plant origin, polymers derived from superficial body growths, egg proteins and latexes of natural origin, and mixtures thereof.

4. The antiwrinkle composition according to claim 3, wherein the latex is selected from the group consisting of from shellac resin, sandarac gum, dammars, elemis, copals, cellulose derivatives and mixtures of these polymers.

5. The antiwrinkle composition according to claim 3, wherein the polymer derived from superficial body growths is selected from the group consisting of chitin, chitosan, hydroxypropylchitosan, the succinylated derivative of chitosan, chitosan lactate, chitosan glutamate, carboxymethylchitosan succinamide, keratin hydrolysates and sulphonic keratins.

6. The antiwrinkle composition according to claim 3, wherein the polymer of plant origin is selected from the group consisting of extracts of cereals, legumes and oilseeds.

7. The antiwrinkle composition according to claim 6, wherein the extract is selected from the group consisting of extracts of maize, rye, wheat, buckwheat, sesame, spelt, pea, broadbean, lentil, soyabean and lupin.

8. The antiwrinkle composition according to claim 1, wherein the polymer contained in said film-forming polymeric system is a synthetic polymer in the form of a latex or pseudolatex.

9. The antiwrinkle composition according to claim 8, wherein the synthetic polymer is selected from the group consisting of anionic, cationic, nonionic or amphoteric polyurethanes, polyurethane-polyacrylics, polyurethane-polyvinylpyrrolidones, polyurethane-polyesters, polyurethane-polyethers, polyureas, acrylic homo- or copolymers, polymers of sulphonated isophthalic acid and mixtures thereof.

10. The antiwrinkle composition according to claim 1, wherein the polymer contained in said film-forming polymeric system is a polymer of synthetic and/or natural origin and contains free hydroxyl groups or anionic groups.

11. The antiwrinkle composition according to claim 1, wherein the polymeric system further comprises a plasticizing agent.

12. The antiwrinkle composition according to claim 1, wherein the dendritic polymer having terminal hydroxyl functional groups is a highly branched polyester macromolecule comprising:
    a central molecule derived from an initiator compound carrying one or more hydroxyl functions (a), and
    chain-extension units derived from a chain-extension molecule carrying a carboxyl function (b) and at least two hydroxyl functions (c), wherein each of the hydroxyl functions (a) of the central molecule is the starting point of a polycondensation reaction (polyesterification) which starts with the reaction of the hydroxyl functions (a) of the central molecule with the carboxyl functions (b) of the chain-extension molecules, and then continues with the reaction of the carboxyl functions (b) with the hydroxyl functions (c) of the chain-extension molecules.

13. The antiwrinkle cosmetic composition according to claim 12, wherein the initiator compound carrying one or more hydroxyl functions forming the central molecule is selected from the group consisting of (a) a monofunctional alcohol, (b) an aliphatic, cycloaliphatic or aromatic diol, (c) a triol, (d) a tetrol, (e) a sugar alcohol, (f) anhydro-ennea-heptitol or dipentaeryritol, (g) an α-alkylglycoside, (h) a polyalkoxylated polymer obtained by polyalkoxylation of one of the alcohols (a) to (g), having a molar mass at most equal to 8000.

14. The antiwrinkle cosmetic composition according to claim 12, wherein the initiator compound is selected from the group consisting of ditrimethylolpropane, ditrimethylolethane, dipentaeyritol, pentaeythritol, an alkoxylated pentaerythritol, trimethylolethane, trimethylolpropane, an alkoxylated trimethylolpropane, glycerol, neopentyl glycol, dimethylolpropane or 1,3-dioxane-5,5-dimethanol.

15. The antiwrinkle cosmetic composition according to claim 12, wherein the chain-extension molecule is selected from the group consisting of:

monocarboxylic acids containing at least two hydroxyl functions, and monocarboxylic acids containing at least two hydroxyl functions of which one or more carry a hydroxyalkyl substituent.

16. The antiwrinlde composition according to claim 15, wherein the chain-extension molecule is selected from the group consisting of dimethylolpropionic acid, α,α-bis(hydroxymethyl)butyric acid, α,α,α-tris(hydroxymethyl) acetic acid, α,α-bis(hydroxymethyl)valeric acid, α,α-bis(hydroxy)propionic acid and 3,5-dihydroxybenzoic acid.

17. The antiwrinkle composition according to claim 12, wherein the initiator compound is selected from the group consisting of ditrimethylolpropane, trimethylolpropane, an ethoxylated pentaerythritol, pentaerythritol or glycerol, and wherein the chain-extension molecule is dimethylolpropionic acid.

18. The antiwrinkle composition according to claim 12, wherein at least one of the terminal hydroxyl functions of the polyester-type dendritic polymer carry substituents derived from at least one chain-terminating agent.

19. The antiwrinkle composition according to claim 1, wherein the concentration of the dendritic polymer relative to the total composition is 0.1 to 5% by weight.

20. The antiwrinkle composition according to claim 1, wherein the film-forming polymeric system is present in an amount of 0.5 to 70% by weight, expressed as active material relative to the total composition.

21. The antiwrinkle composition according to claim 1, wherein the weight ratio of the dendritic polymer to the film-forming polymeric system is within the interval ranging from 1/2 to 1/100.

22. The antiwrinkle composition according to claim 1, further comprising one or more cosmetic active ingredients selected from the group consisting of anti-free radical agents, moisturizing agents, vitamins, proteins other than the tightening polymers, ceramides, α-hydroxy acids, β-hydroxy acids and retinoids.

23. The antiwrinkle composition according to claim 1, further comprising at least one adjuvant selected from the group consisting of solvents, pH-regulating agents, antioxidants, preservatives, pigments and colourings, fillers, emollients, antifoams, vegetable or animal oils or waxes, silicones, perfumes, surfactants, plasticizers, thickening or gelling polymers and sunscreens.

24. The antiwrinkle composition according to claim 1, which is in the form of an emulsion, a cream or a milk, a gel, a lotion, a vesicular dispersion, a serum, a paste or a solid stick.

25. A method of treatment of the skin, comprising applying to the skin of the face, the neck and/or the cleavage the antiwrinkle composition according to claim 1.

26. A cosmetic, comprising the antiwrinkle composition of claim 1 for reducing and/or removing the wrinkles and/or fine lines on the skin by a tightening effect.

27. A method for the preparation of a cosmetic or dermatological composition intended for reducing and/or removing the wrinkles and/or fine lines on the skin, comprising combining:

a dispersion of a film-forming polymeric system comprising at least one polymer capable of forming a film permeable to water vapour, having a Young's modulus ranging from $10^8$ to $9 \times 10^{10}$ N/m$^2$ and producing, after application at a concentration of 7% in water and then drying, a retraction of the isolated *stratum corneum* greater than 1% at a temperature of 30° C. and a relative humidity of 40%, and a dendritic polyester polymer having terminal hydroxyl functional groups, to prepare a cosmetic or dermatological composition intended for reducing and/or removing the wrinkles and/or fine lines on the skin.

* * * * *

UNITED STATES PATENT AND TRADEMARK OFFICE
CERTIFICATE OF CORRECTION

PATENT NO.    : 6,284,233 B1
DATED         : September 4, 2001
INVENTOR(S)   : Simon et al.

It is certified that error appears in the above-identified patent and that said Letters Patent is hereby corrected as shown below:

Column 11,
Line 28, "ditrimethylolethane, dipentaeyritol, pentaeythritol, an..." should read -- ditrimethylolethane, dipentaerythritol. pentaerythritol, an..." --

Signed and Sealed this

Twenty-sixth Day of March, 2002

Attest:

Attesting Officer

JAMES E. ROGAN
Director of the United States Patent and Trademark Office